(12) United States Patent
Viscogliosi et al.

(10) Patent No.: US 9,351,843 B2
(45) Date of Patent: May 31, 2016

(54) SYSTEMS AND METHODS FOR JOINT REPAIR INCLUDING SUBCHONDRAL TREATMENT OF BONE

(71) Applicant: ZIMMER KNEE CREATIONS, INC., Exton, PA (US)

(72) Inventors: Marc R. Viscogliosi, New York, NY (US); Shaun B. Hanson, West Chester, PA (US); David L. Nichols, West Chester, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 96 days.

(21) Appl. No.: 14/207,834

(22) Filed: Mar. 13, 2014

(65) Prior Publication Data

US 2014/0277544 A1 Sep. 18, 2014

Related U.S. Application Data

(60) Provisional application No. 61/784,527, filed on Mar. 14, 2013.

(51) Int. Cl.
*A61F 2/38* (2006.01)
*A61B 17/34* (2006.01)
*A61B 17/00* (2006.01)
*A61F 2/30* (2006.01)
*A61F 2/28* (2006.01)
*A61F 2/46* (2006.01)

(52) U.S. Cl.
CPC ............. *A61F 2/389* (2013.01); *A61B 17/3472* (2013.01); *A61B 2017/0073* (2013.01); *A61F 2/30744* (2013.01); *A61F 2002/2835* (2013.01); *A61F 2002/30332* (2013.01); *A61F 2002/30677* (2013.01); *A61F 2002/30878* (2013.01); *A61F 2002/30901* (2013.01); *A61F 2002/30902* (2013.01); *A61F 2002/4631* (2013.01)

(58) Field of Classification Search
CPC . A61F 2/389; A61F 2/30744; A61F 2/30723; A61F 2002/4631; A61B 17/3472; A61B 17/8808; A61B 2017/564
See application file for complete search history.

(56) References Cited

U.S. PATENT DOCUMENTS

| 4,815,454 | A | * | 3/1989 | Dozier, Jr. | A61B 17/8808 606/94 |
|---|---|---|---|---|---|
| 5,980,527 | A | * | 11/1999 | Cohen | A61B 17/8808 606/92 |
| 8,062,364 | B1 | | 11/2011 | Sharkey et al. | |
| 8,608,802 | B2 | | 12/2013 | Bagga et al. | |
| 2011/0125156 | A1 | | 5/2011 | Sharkey et al. | |
| 2011/0125157 | A1 | | 5/2011 | Sharkey et al. | |
| 2012/0259312 | A1 | * | 10/2012 | Iannotti | A61B 17/8802 604/506 |

* cited by examiner

*Primary Examiner* — Brian Dukert
(74) *Attorney, Agent, or Firm* — Schwegman Lundberg & Woessner, P.A.

(57) ABSTRACT

Systems and methods for the treatment of a joint are provided. These systems and methods may also include a subchondral treatment of bone of the same joint. These joint treatment methods may be non-surgical or surgical. Also provided are devices and instruments associated with the methods.

9 Claims, 6 Drawing Sheets

SYSTEMS AND METHODS FOR JOINT REPAIR INCLUDING SUBCHONDRAL TREATMENT OF BONE

CLAIM OF PRIORITY

This application claims the benefit of U.S. Provisional Patent Application Ser. No. 61/784,527, filed on Mar. 14, 2014, which is incorporated by reference herein in its entirety.

FIELD

The present invention relates to methods for treating joint pain, and associated devices and instruments for such pain treatment. More particularly, the present invention relates to methods for the non-surgical and surgical treatment of joints to alleviate pain resulting from damage or disease, such as osteoarthritis. Even more particularly, the methods can include a combination of joint treatments, including subchondral treatment of bone.

BACKGROUND

Human joints, in particular the knee, hip, ankle, shoulder, and spine, are susceptible to degeneration from disease, trauma, and long-term repetitive use that eventually lead to pain. Knee pain, for example, is the impetus for a wide majority of medical treatments and associated medical costs. Osteoarthritis (OA or degenerative arthritis) is the most common joint disorder known. Osteoarthritis is characterized by cartilage loss at the joint, and symptoms generally include pain and stiffness. The disease can affect all joints of the body, including the hip, shoulder, ankle, and spine, to name a few. One form of the disorder, osteoarthritis of the knee, is a common and rapidly growing problem amongst U.S. adults. Knee osteoarthritis often causes severe pain and is associated with loss of function leading to a diminished quality of life. Knee osteoarthritis can be defined by the thinning, softening, fissuring, fibrillation, and eventual loss, of cartilage covering the surface of the bones in the knee joint. In the early stages of the disease process, this loss of cartilage may cause minimal pain and often those afflicted are asymptomatic. Unfortunately, the natural history of knee OA usually is progressive, leading to the significant symptoms and problems already described.

Patients most often seek treatment because of pain and deterioration of quality of life attributed to the osteoarthritis. The main goal of osteoarthritis treatments is to reduce or eliminate pain, and restore normal joint function. Both non-surgical and surgical treatments are currently available for this purpose, with the appropriate treatment being selected based in part on the stage and/or severity of the disease.

Non-surgical treatments for knee osteoarthritis include weight loss (for the overweight patient), activity modification (low impact exercise), quadriceps strengthening, patellar taping, analgesic and anti-inflammatory medications, injections, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

One type of surgical treatment focuses on unloading forces from the damaged joint. Another type of surgical treatment aims to replace, either partially or wholly, the damaged area of the joint. For example, one surgical treatment seeks to replace the damaged or worn cartilage by way of cartilage resurfacing or cartilage replacement. Other surgical treatments, such as high tibial osteotomy (HTO) or total knee replacement (TKR) or arthroplasty (TKA), are often recommended for patients with severe pain associated with osteoarthritis, especially when other non-invasive options have failed. Both procedures have been shown to be effective in treating knee pain associated with osteoarthritis, at least in the short term.

These treatments are based on the popular theory within the medical community that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. However, the severity of osteoarthritis, especially in the knee, has been found to correlate poorly with the incidence and magnitude of knee pain. Because of this, surgeons and medical practitioners have struggled to deliver consistent, reliable pain relief to patients, especially if preservation of the joint is desired.

In some instances, the joint pain recurs in patients after partial or total joint replacement surgery after some time. This is generally believed to be due to the disease state advancing beyond the benefits of the initial joint replacement treatment. Accordingly, better treatment options are still needed for patients suffering from joint pain, particularly due to osteoarthritis and other degenerative diseases, to address the various stages of the disease and provide a more complete treatment over the continuum of the disease's natural progression.

SUMMARY

In general, the present disclosure provides embodiments related to systems and methods for the treatment of a joint, wherein the methods include a subchondral treatment of the subchondral region of the joint and performed in combination with other non-surgical or surgical treatments to repair the joint. Devices and instruments associated with the methods are also provided.

In one exemplary embodiment, a method of treating a joint is provided. The method may comprise performing a primary treatment on a bone of the joint, and performing a secondary treatment in a subchondral region of the same bone, the secondary treatment comprising stabilizing and/or reinforcing the subchondral region for example to enhance strength of the subchondral region. The primary treatment may comprise a surgical treatment, such as an arthroscopy, partial joint repair, total joint repair, microfracture treatment, cartilage resurfacing, cartilage regeneration, cartilage replacement, meniscal tear repair, or a torn ligament repair. Other primary treatments may also include a partial joint replacement revision, or a total joint replacement revision. Alternatively, the primary treatment may comprise a non-surgical treatment such as an intra-articular injection of an injectable material to treat articular cartilage damage. The injectable material comprises bone morphogenic protein (BMP), stem cells, or platelet rich plasma (PRP).

The secondary treatment may be performed intraoperatively in conjunction with the primary treatment, or the secondary treatment may be performed postoperatively after the primary treatment. The secondary treatment may comprise creating subchondral access to the subchondral region of the bone, and may further include the step of implanting in the subchondral region of the bone at least one reinforcing member via the subchondral access. Alternatively, or in addition to the step of implanting, the secondary treatment may further include the step of injecting into the subchondral region of the bone a bone hardening or other injectable material via the subchondral access.

In one exemplary embodiment, a system for treating a joint such as a knee, hip, ankle, shoulder, etc. joint is provided. The system may comprise a disposable or non-disposable base member such as a plate and an integral or non-integral extension like a stem, needle, peg or screw extending from the base member. The base member includes a port for injection of an injectable material therethrough into the extension. The extension is cannulated and includes one or more openings to its exterior that are in fluid communication with the port. The system can also include a sealing member such as a bolt for sealing the port. The extension may be configured to disperse the injectable material into a subchondral region of a resected bone such as a proximal tibia against which the base member is positioned. In addition, the extension may further include an exterior groove within which the one or more openings reside.

In another exemplary embodiment, a system for treating a knee joint is provided. The system may comprise a proximal tibial implant that includes a baseplate and a stem extending therefrom. The baseplate includes a port for injection of an injectable material therethrough into the stem. The stem is cannulated and includes one or more openings to its exterior that are in fluid communication with the port. The system also includes a sealing member such as a screw for sealing the port. The stem may be configured to disperse the injectable material into a subchondral region of a resected proximal tibia. In addition, the stem may further include an exterior groove within which the one or more openings reside.

In still another exemplary embodiment, a system for treating a knee joint is provided. The system may comprise a proximal tibial implant that includes a baseplate and a stem extending therefrom. The baseplate includes one or more passages for injection of an injectable material therethrough. The system further includes one or more cannulated screws each for insertion into one of the one or more passages in the baseplate. The screws further include one or more exterior openings for dispersal of the injectable material. The one or more cannulated screws may further include a groove within which the one or more exterior openings reside. The exterior openings of the one or more cannulated screws may be configured to disperse the injectable material in a subchondral region of a resected proximal tibia.

In yet another exemplary embodiment, a system for treating a joint is provided. The system may comprise a disposable injection cap having a holding pin for insertion into a resected bone surface, and one or more ports for injection of material therethrough; and a cannulated injection needle for insertion into the one or more ports, the needle further including a plurality of openings for dispersal of material therethrough. The holding pin may be removable from the injection cap, or the holding pin may be integral with the injection cap.

In still yet another embodiment, a system for treating a joint is provided. The system may comprise an implantable base stem for insertion into a resected bone of the joint, the stem including a tapered neck, the stem being cannulated and including one or more openings to its exterior; an injection cap having a distal hub with an opening therein for receiving the tapered neck of the base stem, and a port for injection of material therethrough, the port aligning with the base stem when the cap is attached to the stem; wherein the port is configured to attach to an injection system. The base stem may further include a groove within which the one or more openings reside. The one or more openings of the base stem may be configured to disperse the injectable material in a subchondral region of the resected bone.

The system may further include an implantable plate having a distal hub with an opening therein for receiving the tapered neck of the base stem, and a sealing screw to attach the plate to the stem. The injection cap may be disposed after injection has occurred.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1:
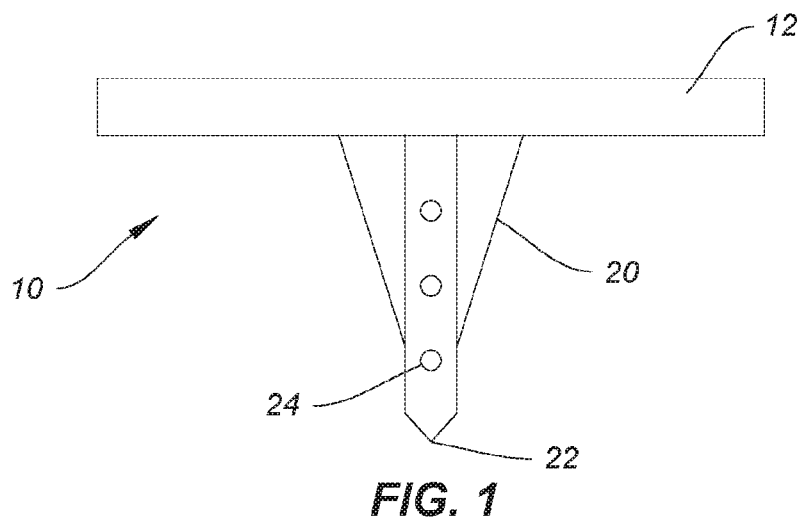
FIG. 1 shows a front view of an exemplary embodiment of a tibial baseplate of the present disclosure.

Methods, devices and instruments for treating joint pain to restore natural joint function and preserving, as much as possible, the joint's articular and cartilage surface are known. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,364 entitled "OSTEOARTHRITIS TREATMENT AND DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In an SCP™ procedure, bone fractures or non-unions are stabilized, integrated or healed, which results in reduction of a bone defect, such as a bone marrow lesion or edema. In addition, the SCP™ procedure restores or alters the distribution of forces in a joint to thereby relieve pain. The SCP™ procedure can be performed arthroscopically or percutaneously to treat pain by stabilizing chronic stress fracture, resolving any chronic bone marrow lesion or edema, and preserving, as much as possible, the articular surfaces of the joint. The SUBCHONDROPLASTY™ procedure generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for the SCP™ procedure for the different extents of treatment needed can be employed. Accordingly, a medical practitioner may elect to use the techniques and devices described herein to subchondrally treat any number of bone defects, as he deems appropriate.

Detection and identification of the relevant bone marrow lesion or bone marrow edema (BML or BME) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

The SCP™ treatment may continue after surgery. In particular, the patient may be monitored for a change in pain scores, or positive change in function. For example, patients are also checked to see when they are able to perform full weight-bearing activity and when they can return to normal activity. Of note, the SCP™ procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP™ treated area may remain undisturbed while the additional treatment is performed, such as where cartilage resurfacing is desired. Alternatively, the SCP™ treated area can be removed, and not create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement.

Various surgical treatments to address subchondral defects known as bone marrow lesions have previously been attempted. Between May and November 2008, three (3) surgeries were performed at Riddle Hospital in Media, Pa. in the United States. On May 12, 2008, Dr. Peter F. Sharkey performed a right knee arthroscopy with arthroscopically assisted stabilization of a patient's right knee with a medial tibial plateau fracture. During the procedure, a cannulated bone biopsy needle was placed into the bone under fluoroscopic guidance, and augmentation material was injected.

The injected augmentation material was Stryker Orthopedics Hydroset (Bone Substitute Material). The surgeon expressed difficulty in injecting the bone substitute material.

On Oct. 27, 2008, Dr. Steven B. Cohen performed a left knee arthroscopy, partial medial meniscectomy, drilling of osteochondral lesion using retrograde technique, and debridement chondroplasty of patellofemoral chondrosis on a patient's left knee with medial meniscus tear and left knee osteochondral defect with bone marrow lesion of the medial femoral condyle. During the procedure, an Anterior Cruciate Ligament (ACL) portal-creation device was repurposed for this surgery. The tibial probe was placed on the medial femoral condyle, with the tunnel guide secured proximally on the thigh. The surgeon expressed difficulty in positioning and stabilizing the guide. A cannulated pin was placed through the tunnel guide and placed distally into the medial femoral condyle. No implantable material was injected into the bone in this case.

On Nov. 10, 2008, Dr. Steven B. Cohen performed a right knee arthroscopic-assisted repair of a tibial plateau fracture bone marrow lesion with subchondral fracture using bone cement, partial medial and partial lateral meniscectomy to treat medial meniscus tear, and arthroscopic debridement and chondroplasty of medial, lateral, and patellofemoral compartments to treat compartment chondrosis. During the procedure, a guide pin was inserted into the medial tibial plateau, and an endo button drill bit was used to expand the drill hole. One (1) cubic centimeter (cc) of cement was inserted into the bone. A second drill hole was made from below, and a second cubic centimeter (cc) of cement was inserted into the bone.

The experiences gained from these previous surgeries helped to develop the fundamental theories underlying the SUBCHONDROPLASTY™ procedure and the number of treatment modalities, associated devices, instruments and related methods of use for performing the SUBCHONDROPLASTY™ procedure, which are disclosed in the aforementioned publications. These treatment modalities may be used alone or in combination, as will be described in detail below. In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Suitable implantable fixation devices for the surgical treatment of these altered bone regions or bone defects, especially at the subchondral level, are known. These devices and instruments can be use in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out or degenerate locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, restoration of normal physiologic stress distribution can be achieved in load bearing joints such as the hip and knee, and mechanical congruity restored, thereby resulting in healing of the inflammation and reduction or elimination of pain.

One of the benefits offered by the SCP™ procedure is that the procedure allows for optional further treatment in the event that a patient requires or desires a joint replacement or other type of joint pain relieving procedure. The subchondral treatment described herein does not exclude a future joint repair or replacement treatment to be applied, and thus may also be performed in conjunction with other procedures. For example, total knee replacements (TKR) or total knee arthroplasties (TKA), partial knee replacements, arthroscopies, meniscal tear repairs, torn ligament repairs, microfracture treatments, cartilage resurfacing, regeneration or replacement, and other types of joint repairs are combinable with a subchondral treatment to stabilize and enhance the strength of the subchondral bone, either as a prophylactic approach or as a targeted treatment of an existing subchondral defect. In fact, the principles of SCP™ can be applied in a combination of therapies to address a number of problems arising from the disease state, either sequentially or in parallel, at one time or over a duration of time. That is, the SCP™ treatment may be performed intraoperatively along with the other joint treatment, or it may be done postoperatively as an adjunct to the primary joint repair treatment.

For instance, in one example, the SCP™ treatment may continue after surgery. In those patients where additional treatment is desired, the SCP™ treated area may remain undisturbed while the additional treatment is performed, such as where cartilage resurfacing is desired. Alternatively, the SCP™ treated area can be removed, so as not to create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement. In other examples, the SCP™ treatment may be combined other non-surgical treatments such as injections.

In general, the present disclosure provides embodiments related to methods for the treatment of a joint, wherein the methods also include a subchondral treatment of the subchondral region of the same joint. These joint treatment methods may be non-surgical or surgical. Devices and instruments associated with the methods are also provided.

In one exemplary embodiment, a method of combining treatment of subchondral bone and articular cartilage is provided. In the exemplary method, an SCP™ treatment as described above can be combined with a non-surgical injection. The injection may comprise bone morphogenic protein (BMP), stem cells, platelet rich plasma (PRP), or another biological agent to stimulate cellular activity and promote cartilage regrowth. This exemplary method provides a two-fold treatment plan in which the first component involves subchondral stabilization while the second component involves articular cartilage repair. By subchondral stabilization, what is meant is the treatment modalities described above with respect to SCP™ techniques including injection of a bone hardening material such as bone substitute material, or implanting a device into the subchondral region of the bone, or both, to mechanically stabilize the subchondral bone. The two components may be administered at the same time, i.e., subchondral bone treatment to heal the subchondral defect such as the BML or BME and intra-articular injection in one process. Alternatively, the two components of the treatment plan may be administered separately at different time intervals during the treatment process.

In another exemplary embodiment, a method combining a subchondral treatment with a total knee replacement (TKR) is provided. Associated implantable devices and instruments configured to combine the treatments may be provided as well. The method and associated devices may be described with reference to FIGS. 1 to 11 which are directed to tibial plate replacement or repair. Of course, the methods and associated devices are applicable to other repairs of the knee, and it is understood that the devices can be easily configured for femoral repair, acetabular cup repair, hip repair, uni-compartmental knee replacement (such as, for example, by halving the tibial components shown and described herein), and other joint resurfacing or joint replacement treatments. Additionally, the principles of these combination treatments may also be applicable in cases of partial or total joint replacement revisions.

Figure 2:
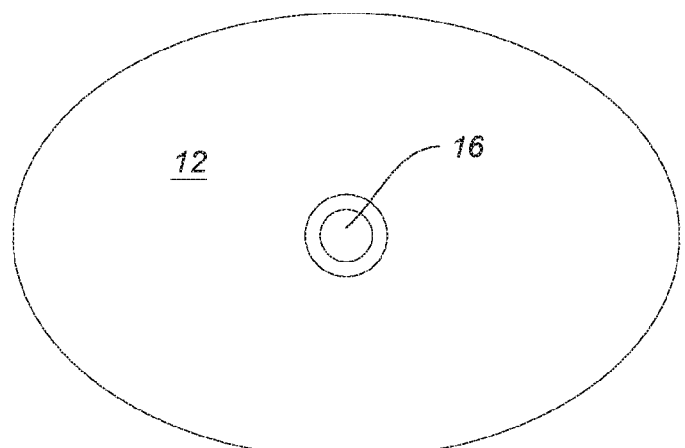
FIG. 2 is a top-down view of the tibial baseplate of FIG. 1.
Figure 3:
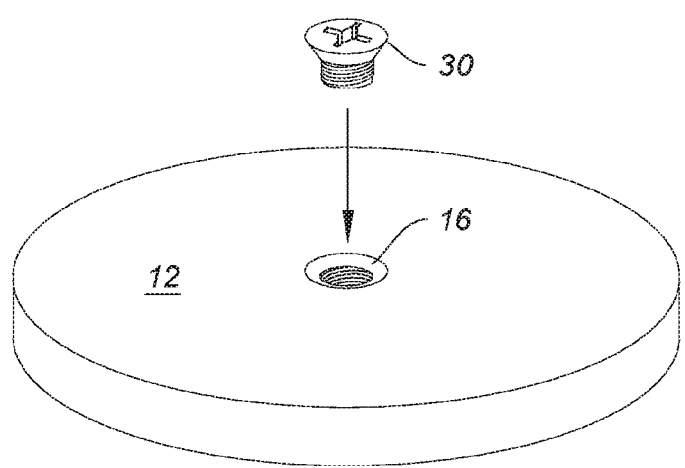
FIG. 3 is a perspective view of the tibial baseplate of FIG. 1 with a sealing screw.

Turning now to the drawings, FIGS. 1-3 show an exemplary embodiment of a tibial baseplate 10 of the present disclosure. The tibial baseplate 10 may be configured for use in a total knee replacement. As shown in FIG. 1 from this front view, the baseplate 10 comprises a plate 12 from which extends a stem 20. The stem 20 may be fenestrated, with one or more openings 24 extending the length of the stem 20. The stem 20 may include a tapered tip 22. This tapered tip 22 may be configured to be sufficiently sharp to pierce bone tissue for ease of insertion, if so desired.

FIG. 2 shows a top view of the plate 12. The plate 12 may have an injection port 16 that extends into the stem 20 such that the port 16 is in fluid communication with the one or more holes 24 of the stem 20. The port 16 may be threaded, as shown in FIG. 3, to receive a screw 30 for closure of the port 16. The port 16 may also be configured with a LuerLok for connection with a syringe or injection system.

In one exemplary embodiment, the method of treating joint pain comprises resecting the top of a tibial bone, and inserting the tibial baseplate 10 into the bone such that the distal stem 20 is fully inserted into the length of the bone while the plate 12 is seated flush against the resected tibial bone surface. Next, a bone substitute material may be injected through the portal 16 of the baseplate 10, into the distal stem 20 and out the openings 24. The bone substitute material would be released below the baseplate 10, into the tibial bone, at or near a subchondral region of the bone. This process is thus similar to the subchondral treatment described above for stabilizing and/or stimulating the subchondral region of a bone.

After injection through the port 16, the port 16 may be sealed with a screw 30, as shown in FIG. 3. This sealing prevents migration of particles between the barriers, i.e., bone substitute material to the joint or ultra high molecular weight polyethylene (UHMWPE) to bone.

Figure 4:
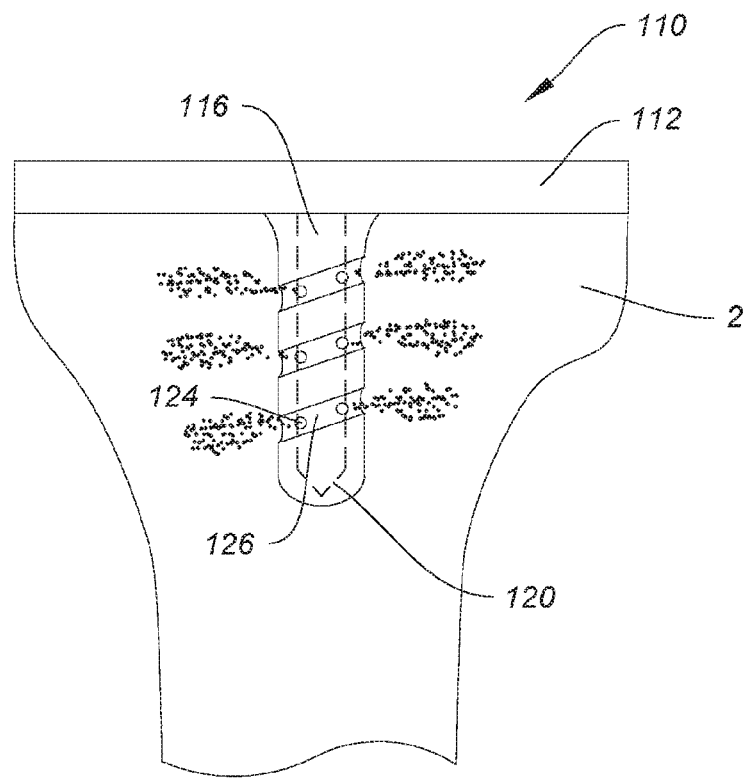
FIG. 4 is a partial cross-sectional view of another exemplary embodiment of a tibial baseplate of the present disclosure in situ.

FIG. 4 shows another exemplary embodiment of a tibial baseplate 110 of the present disclosure. The baseplate shares similar features to the baseplate 10 previously described, with similar features or elements sharing the same reference numeral following the prefix "1". Tibial baseplate 110 comprises a plate 112 from which extends a distal stem 120. Similar to distal stem 20, the distal stem 120 may be fenestrated and include openings 124. In addition, the distal stem 120 may comprise flutes or grooves 126 within which the openings 124 reside. In one embodiment, the groove 126 may be a spiral groove, as shown. However, it is understood that other groove configurations may be utilized, and in fact more than one groove or flute 126 may be provided. Likewise, the distal stem 120 may be configured with any size and length appropriate for the tibial bone to be treated. The locations of the openings 124 within the grooves 126 can similarly vary in number and configuration. The plate 112 of tibial baseplate 110 comprises a central port 116 in fluid communication with these openings 124. The port 116 may be configured with a LuerLok for connection with a syringe or injection system. And similar to port 16, the port 116 may include a threaded opening for sealing with a screw.

Tibial baseplate 110 can be used in a similar method as described for tibial baseplate 10. After resecting the top of a tibial bone 2, the tibial baseplate 110 can be inserted into the bone 2 such that the distal stem 120 is fully inserted into the length of the bone 2 while the plate 112 is seated flush against the resected tibial bone surface. Next, a bone substitute material may be injected through the portal 116 of the baseplate 110, into the distal stem 120 and out the openings 124. Since the openings 124 reside within groove 126, the bone substitute material can be directionally guided to predetermined areas along the length of the bone during the injection. After injection through the port 116, the port 116 may be sealed with a screw.

Figure 5:
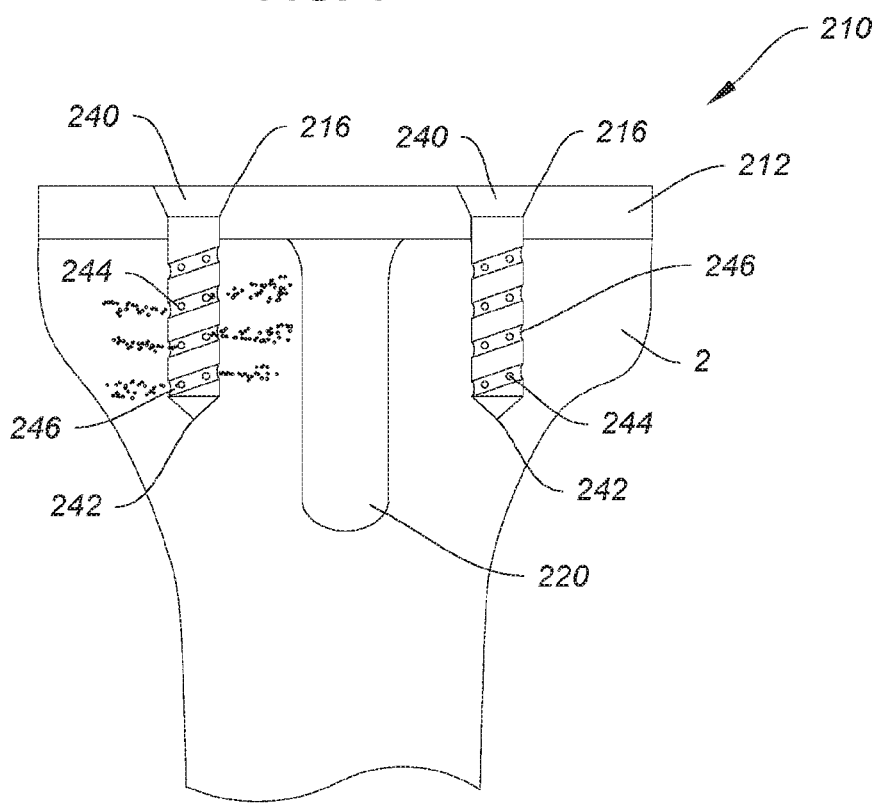
FIG. 5 is a partial cross-sectional view of still another exemplary embodiment of a tibial baseplate of the present disclosure in situ.

FIG. 5 shows still another exemplary embodiment of a tibial baseplate 210 of the present disclosure. The baseplate shares similar features to the baseplate 10 previously described, with similar features or elements sharing the same reference numeral following the prefix "2". Tibial baseplate 210 comprises a plate 212 from which extends a distal stem 220. However, unlike the previous embodiments the distal stem 220 is not fenestrated although it could be in an alternative embodiment. Instead, the plate 212 may include one or more screw holes 216 for receiving a fenestrated screw 240. The fenestrated screw 240 may have a sharp tip 242 and a groove 246 extending along its length. Within the groove 246 are openings 244 that are in fluid communication with a port (not shown) atop the screw 240. The screw 240 may be of a type previously described in co-owned U.S. Pat. No. 8,608, 802, filed Nov. 19, 2010 and entitled "IMPLANTABLE DEVICES FOR SUBCHONDRAL TREATMENT OF JOINT PAIN," and co-owned and co-pending U.S. patent application Ser. No. 12/950,183, filed Nov. 19, 2010 and entitled "BONE-DERIVED IMPLANTABLE DEVICES FOR SUBCHONDRAL TREATMENT OF JOINT PAIN," the contents of which are herein incorporated in their entirety by reference.

Tibial baseplate 210 can be used in a similar method as described for tibial baseplates 10, 110. After resecting the top of a tibial bone 2, the tibial baseplate 210 can be inserted into the bone 2 such that the distal stem 220 is fully inserted into the length of the bone 2 while the plate 212 is seated flush against the resected tibial bone surface. Next, fenestrated screws 240 may be inserted into the screw holes 216 in the plate 212. Then, a bone substitute material may be injected through the fenestrated screws 240 and out the openings 244. Since the openings 244 reside within groove 246, the bone substitute material can be directionally guided to predetermined areas along the length of the bone during the injection. Accordingly, the fenestrated screws 240 offer multiple functions. The screws 240 not only help anchor the plate 212 to the resected bone surface, but the screws 240 act as injection ports for the delivery of bone substitute material into the bone 2, as well as seal up the holes 216 to prevent material from escaping.

Figure 6:
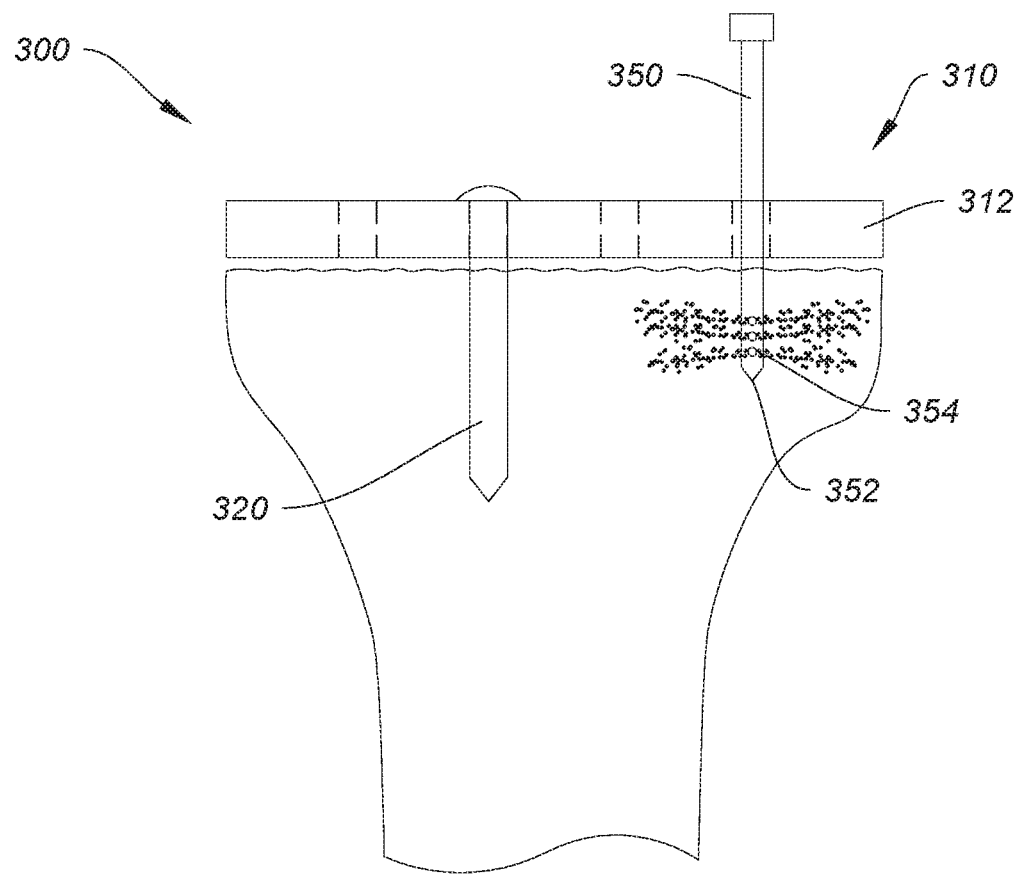
FIG. 6 is a partial cross-sectional view of an exemplary embodiment of an injection cap system of the present disclosure in situ.
Figure 7:
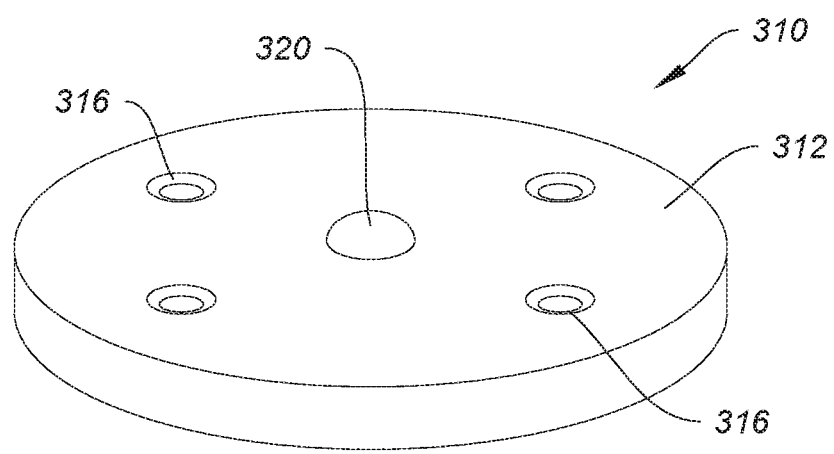
FIG. 7 is a perspective view of the top of the injection cap of FIG. 6.
Figure 8:
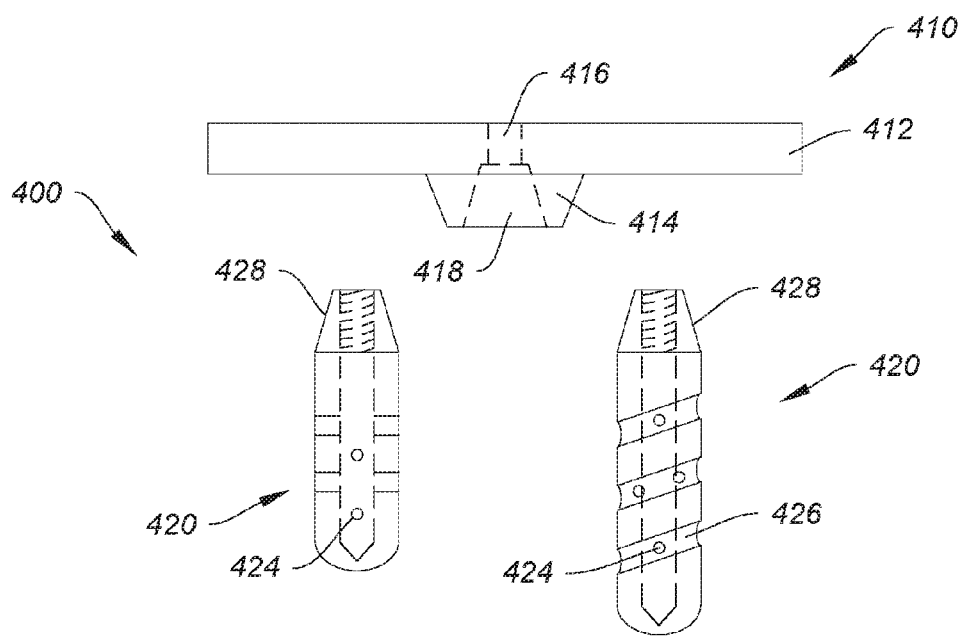
FIG. 8 is an exploded view of an exemplary embodiment of a modular baseplate and injection system of the present disclosure.

FIGS. 6 and 7 shows an exemplary embodiment of a tibial injection guide system 300 of the present disclosure. The system 300 may comprise an injection cap 310 having a plate 312 that can be used prior to insertion of a tibial baseplate onto a resected tibial bone 2. The system 300 may further comprise a holding pin 320 and the plate 312 may comprise a plurality of injection ports 316. The holding pin 320 may be removable, and inserted through an opening on the plate 312, or the holding pin can be integral to the plate 312. The cap 310 may be formed of a plastic, such as a polyetheyene like an ultra high molecular weight polyethylene (UHMWPE), for example, and be disposed after use.

In use, the injection cap 310 is placed over the resected tibial bone surface. The cap 310 can be temporarily anchored to the bone 2 with holding pin 320. Next, bone substitute material may be directly injected through the injection ports 316 in a manner similar to that previously described. In one example, the injection ports 316 may be configured for attachment to a syringe or injection system. In another example, the system 300 may be provided with injection needles 350 as shown in FIG. 6. The injection needle 350 may comprise a sharp tip 352 and a plurality of openings 354 along a length of the needle 350. The injection needle 350 may be placed in one or more of the injection ports 316, and connected to a syringe or injection system to deliver bone substitute material into the bone through these openings 354. After injection of the material, the entire construct may be removed. Thereafter, an implantable tibial baseplate may be placed over the resected tibial bone 2 to complete the total knee replacement therapy.

FIGS. 8-11 show an exemplary embodiment of a modular tibial baseplate and injection system 400 of the present disclosure. As shown in the exploded view of FIG. 8, the system 400 includes an injection cap 410 comprising a base plate 412 with a central opening 416 and a distal hub 414 with an opening 418 for receiving a stem component 420. As shown, the stem components 420 may be fenestrated and provided in a plurality of lengths, with a variety of configuration such as with grooves 426 and openings 424 suitable for injection of bone substitute material into the bone. The stem components 420 have a shaped or tapered neck 428 that fits within the opening 418 of the distal hub 414 of the plate component. This fit could be a friction fit, interference fit, press-fit, or it could be a threaded connection.

Figure 9:
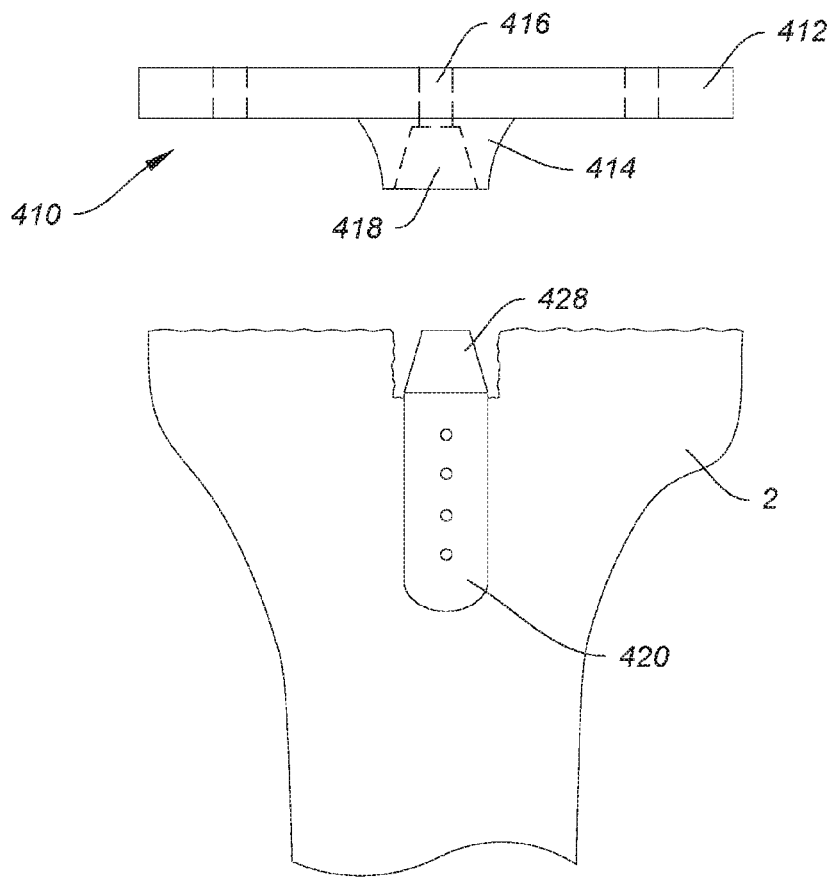
FIG. 9 is an exploded view of the injection cap with stem component of FIG. 8 in situ.

As shown in FIG. 9, in a first step of an exemplary method of use, a distal stem component 420 of the system 400 is selected, and inserted into the tibial bone 2 after resection, or even after removal of an old tibial implant (in the case of a revision surgery) to make way for a new implant if so desired, in a manner similar to the ones previously described and as is performed in known total knee replacement (TKR) surgeries. Next, the base plate 412 is placed over the top of the bone 2 and the injection cap 410 attached to the stem component 420 by way of the tapered neck 428 and opening 418 within distal hub 414.

Figure 10:
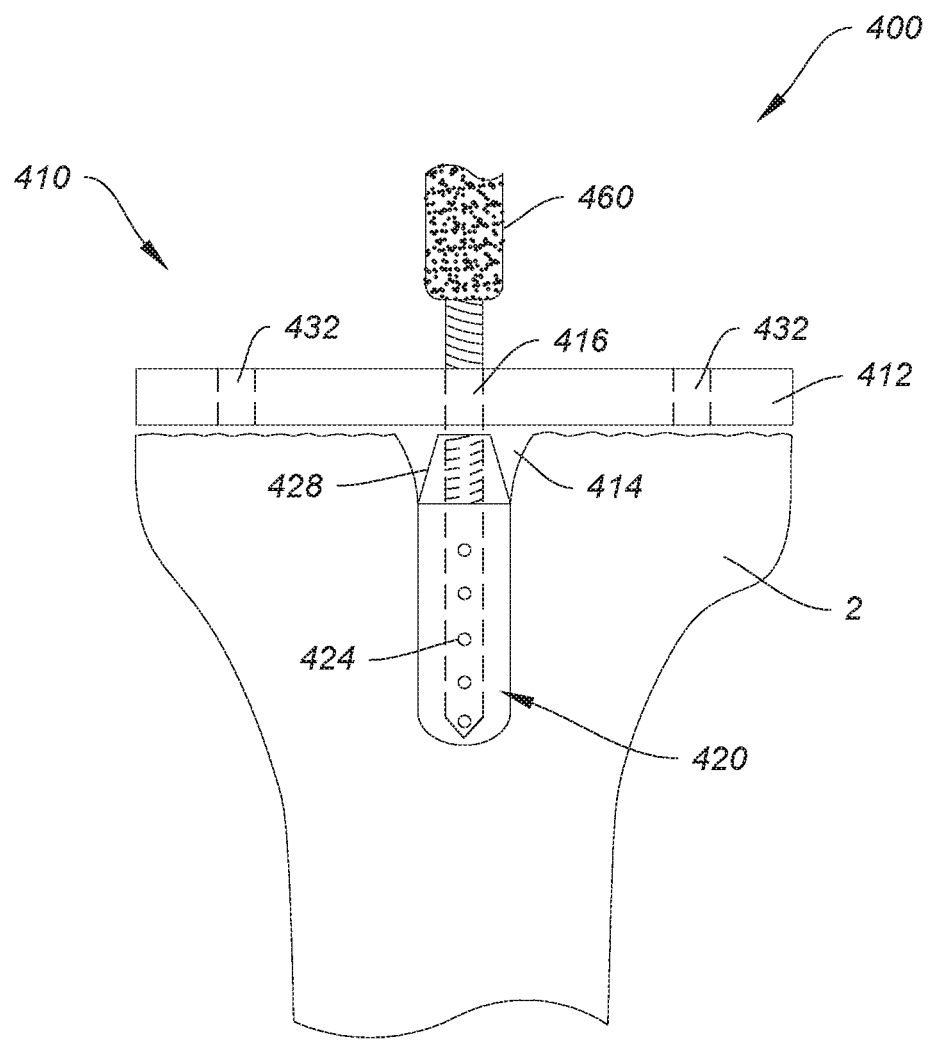
FIG. 10 shows the injection cap and stem component of FIG. 9 attached to a syringe in situ.

After the injection cap 410 is secured to the stem component 420, a syringe 460 or injection system can be attached to the stem component 420 through the opening 416 of the base plate 412 and the opening 418 of the distal hub 414, as shown in FIG. 10. This syringe 460 effectively extends through the base plate 412 and hub 414, and connects to the fenestrated stem component 420 through its tapered neck 428. This connection may be configured as a friction fit, interference fit, press-fit, or it could be a threaded or LuerLok connection. Once the syringe 460 is properly connected, bone substitute material may be injected through the stem component 420 and out the openings 424 into the bone 2.

In use, the base plate 412 serves to hold the bone substitute material inside the bone under pressure. The base plate 412 additionally serves to protect the surface of the modular tapered neck 428 of the stem component 420. As with other TKR systems, it is critical to keep the modular stem tapered neck 428 clean from debris. Optionally, the base plate 412 may also include injection ports 432 for receiving either an injection screw or injection needle, such as those previously described.

After the bone substitute material has been injected, the base plate 412, which can be formed of a plastic, such as a polyetheyene like an ultra high molecular weight polyethylene (UHMWPE), can be removed for disposal. A permanent, or implantable component 440 comprising a base plate 442 with a distal hub 444 similar to the injection cap 410 previously described may be placed over the resected tibial bone 2. The distal hub 444 may be impacted onto the tapered neck 428 of the stem component 420. The connection between the distal hub 444, which also includes an opening 448 to receive the tapered neck 428, may be configured as a friction fit, interference fit, press-fit, or it could be a threaded connection.

Figure 11:
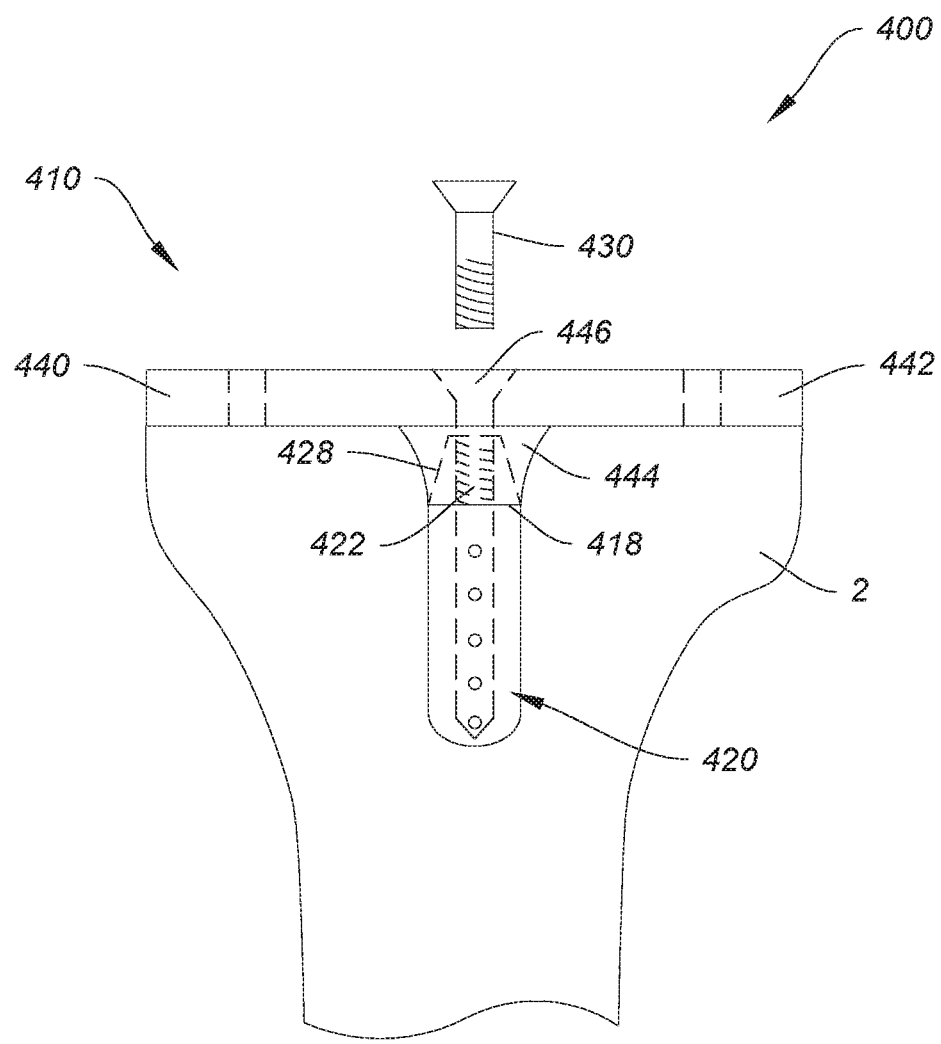
FIG. 11 shows an exploded view of a baseplate and screw for use with the system of FIG. 8 in situ.

To lock the implantable component 440 to the stem component 420, the base plate 442 may include a screw hole 446 to receive a screw 430, as shown in FIG. 11. The screw 430 may be threaded through the base plate 442 and into a threaded port 422 within the tapered neck 428 of the stem component 420. Securing the screw 430 to the base plate 442 locks the implantable component to the stem component while also sealing off the port through the stem component 420.

While some of the methods are described herein as injecting bone substitute material into bone, it is understood that the methods can be practiced without limitation using other injectable materials as well, including bone cement, bone hardening materials, bone void fillers, and other forms of PMMA or calcium phosphate. Furthermore, although the methods are described herein for a knee joint, it is understood that the methods would equally apply to other joints as well, particularly load-bearing joints, and can include hips, shoulders, ankles, and spine.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A method of treating a knee joint, comprising:
resecting a portion of a proximal tibia adjacent the knee joint to form a resected surface of the proximal tibia;
positioning a disposable member over the resected surface of the proximal tibia, wherein the disposable member includes a disposable plate with one or more injection ports that extend through the disposable plate from a top side of the disposable plate to a bottom side of the disposable plate;
injecting an injectable material through the one or more injection ports of the disposable plate and into bone beneath the resected surface of the proximal tibia;
removing the disposable plate from over the resected surface of the proximal tibia; and
implanting a tibial prosthesis in the proximal tibia, wherein said implanting includes placing a tibial baseplate of the tibial prosthesis over the resected surface of the proximal tibia
implanting a cannulated stem component in the proximal tibia, wherein said positioning the disposable member over the resected surface of the proximal tibia includes attaching the disposable plate to the cannulated stem component so that a first injection port in the disposable plate is linked to a cannula of the cannulated stem component, and wherein said injecting includes injecting the injectable material through the first injection port and out of the cannulated stem component into bone beneath the resected surface of the proximal tibia.

2. The method of claim 1, wherein an interference fit attaches the cannulated stem component to the disposable plate.

3. The method of claim 1, wherein said injecting the injectable material out of the cannulated stem component includes injecting the injectable material through an injection device that extends through the disposable plate and attaches to the cannulated stem component.

4. The method of claim 3, wherein said injection device includes a syringe.

5. The method of claim 1, wherein said placing the tibial baseplate of the tibial prosthesis over the resected surface of the proximal tibia includes attaching the tibial baseplate to the cannulated stem component.

6. The method of claim 5, wherein an interference fit attaches the cannulated stem component to the tibial baseplate.

7. The method of claim 6, wherein a screw that extends through the tibial baseplate and that is threaded into the cannulated stem component supplements attachment of the cannulated stem component to the tibial baseplate.

8. The method of claim 5, wherein said attaching the tibial baseplate to the cannulated stem component links a first injection port in the tibial baseplate to the cannula of the cannulated stem component.

9. The method of claim 8, wherein said tibial baseplate includes one or more additional injection ports that extend through the tibial baseplate from a top side of the tibial baseplate to a bottom side of the tibial baseplate.

* * * * *